United States Patent
Singh

(10) Patent No.: US 7,473,916 B2
(45) Date of Patent: Jan. 6, 2009

(54) APPARATUS AND METHOD FOR DETECTING CONTAMINATION WITHIN A LITHOGRAPHIC APPARATUS

(75) Inventor: Mandeep Singh, Delft (NL)

(73) Assignee: ASML Netherlands B.V., Veldhoven (NL)

(*) Notice: Subject to any disclaimer, the term of this patent is extended or adjusted under 35 U.S.C. 154(b) by 235 days.

(21) Appl. No.: 11/303,014

(22) Filed: Dec. 16, 2005

(65) Prior Publication Data

US 2007/0139648 A1 Jun. 21, 2007

(51) Int. Cl.
*H01J 3/14* (2006.01)
(52) U.S. Cl. .................. 250/504 R; 250/492.1; 250/493.1
(58) Field of Classification Search .......... 250/504 R, 250/493.1, 492.1, 492.2, 492.3, 216, 227.14; 430/5; 378/34
See application file for complete search history.

(56) References Cited

U.S. PATENT DOCUMENTS

| | | | |
|---|---|---|---|
| 5,647,030 A * | 7/1997 | Jorgenson et al. ............ 385/12 |
| 5,929,981 A | 7/1999 | Keilbach |
| 6,067,154 A | 5/2000 | Hossain et al. |
| 6,081,328 A | 6/2000 | Eng |
| 6,480,282 B1 * | 11/2002 | Chinowsky et al. ......... 356/445 |
| 6,753,188 B2 * | 6/2004 | Perkins et al. .............. 436/172 |
| 6,784,999 B1 * | 8/2004 | Tao et al. .................... 356/445 |
| 6,795,777 B1 | 9/2004 | Scully et al. |
| 7,078,712 B2 * | 7/2006 | Perel et al. ............. 250/492.21 |
| 7,253,426 B2 | 8/2007 | Gorrell et al. |
| 2003/0179379 A1 * | 9/2003 | Gedig ......................... 356/445 |
| 2005/0133727 A1 * | 6/2005 | Banine et al. ............... 250/397 |
| 2005/0148100 A1 | 7/2005 | Su et al. |
| 2005/0162657 A1 * | 7/2005 | Bahatt et al. ................ 356/445 |
| 2005/0170328 A1 * | 8/2005 | Gunnewijk et al. ............ 435/4 |
| 2005/0206892 A1 | 9/2005 | Wang et al. |
| 2005/0244093 A1 * | 11/2005 | VanWiggeren et al. ........ 385/12 |
| 2006/0066859 A1 * | 3/2006 | Downey ...................... 356/445 |
| 2007/0139646 A1 | 6/2007 | Singh |
| 2007/0222996 A1 * | 9/2007 | Guan et al. ................. 356/445 |

OTHER PUBLICATIONS

Zhang, et al. "Surface plasmon detection of surface contamination of metallic film surfaces" Proceedings of SPIE vol. 777 (1987) p. 162.*
Homola, et al "Surface plasmon resonance sensors: review" Sensors and Actuators B 54 (1999) p. 3-15.*

(Continued)

*Primary Examiner*—Jack I Berman
*Assistant Examiner*—Michael Maskell
(74) *Attorney, Agent, or Firm*—Sterne, Kessler, Goldstein & Fox P.L.L.C.

(57) ABSTRACT

A lithographic apparatus that includes at least one optical surface exposed to a radiation beam, and a surface plasmon resonance measurement apparatus adjacent the optical surface that is configured to detect contamination of at least one optical surface of the lithographic apparatus. The measurement apparatus is located near or in close proximity to the optical surface to as to emulate and determine possible contamination without interfering with the radiation beam used to expose the optical surface. A radiation source for the measurement apparatus is configured to provide a probing beam of radiation having an angle of incidence. By measuring the surface plasmons and/or the angles of incidence of a reference optical surface in the measurement apparatus, contamination deposited on an optical surface in the lithographic apparatus may be inferred.

25 Claims, 3 Drawing Sheets

OTHER PUBLICATIONS

Matsubara, et al "Optical chemical sensor based on surface plasmon measurement" Applied Optics vol. 27 No. 6 Mar. 15, 1988 p. 1160.*

Caruso, et al. "Acousto-optic surface-plasmon resonance measurements of thin films on gold" J. Appl. Phys. 83(2) Jan. 15, 1998 p. 1023.*

Boussaad, et al. "High-resolution multiwavelength surface plasmon resonance spectrocopy for probing conformational and electronic changes in redox proteins" Analytical Chemistry vol. 72 No. 1 Jan. 1, 2000 p. 222.*

Panigrahi, et al. "Optical surface plasmon resonance sensor design" Proceedings of SPIE vol. 3897 Nov.-Dec. 1999 p. 534.*

Kretschmann et al., "Radiative Decay of Non Radiative Surface Plasmons Excited by Light," (1968), pp. 2135-2136.

Liedberg, et al., "Biosensing With Surface Plasmon Resonance — How It All Started," Biosensors & Bioelectronics 10 (1995), pp. i-ix.

Hooper et al., "Making Tunnel Barriers (Including Metals) Transparent", Physical Review Letters, 97 (2006), pp. 053902-1-053902-4.

Otto, "Excitation of Nonradiative Surface Plasma Waves in Silver by the Method of Frustrated Total Reflection," Zeitschrift fur Physik 216 (1968), pp. 398-410.

* cited by examiner

APPARATUS AND METHOD FOR DETECTING CONTAMINATION WITHIN A LITHOGRAPHIC APPARATUS

FIELD

The present invention relates to a lithographic apparatus and a method for detecting contamination within a lithographic apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

To be most effective, the lithographic apparatus is used in as clean an environment as possible. One of the main reasons for using a clean environment is to prevent contamination of the substrate and any optical surfaces which are used to manipulate radiation beams used to apply a desired pattern onto the substrate. For example, a lithographic apparatus using an extreme ultraviolet (EUV) radiation beam is known to generate contaminants which can lead to a deposit forming on the optical surfaces. For example, irradiation of some optical surfaces with EUV is known to cause the build up of a carbonaceous deposit on these optical surfaces. These deposits may reduce the operating resolution of the lithographic apparatus. It is thus desirable to minimize the contamination of optical surfaces and, when necessary, clean the surfaces to remove the deposits. Cleaning of the optical surfaces is undertaken when the level of the contaminant is such that the operation of the lithographic apparatus is compromised. Therefore, detection of the level of contaminants on the optical surfaces is important.

SUMMARY

The present invention provides a new apparatus and method for detecting the level of contamination on optical surfaces of a lithographic apparatus.

According to an aspect of the invention, there is provided a lithographic apparatus comprising at least one optical surface constructed and arranged to be exposed to a radiation beam; and a surface plasmon resonance measurement apparatus configured to detect contamination of the at least one optical surface.

According to an aspect of the invention, there is provided a method of detecting contamination of at least one optical surface of a lithographic apparatus, wherein surface plasmons are used to detect contamination of the at least one optical surface of the lithographic apparatus.

According to an aspect of the invention, there is provided a surface plasmon resonance measurement apparatus arranged to detect contamination of at least one optical surface of a lithographic apparatus.

According to an aspect of the invention, there is provided an apparatus arranged to detect contamination of an optical surface comprising: a surface plasmon generator arranged to generate a surface plasmon mode in the optical surface; a waveguide located adjacent the optical surface and arranged such that the surface plasmon mode may be coupled into the waveguide and converted into a photon; and a detector arranged to detect the photon.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
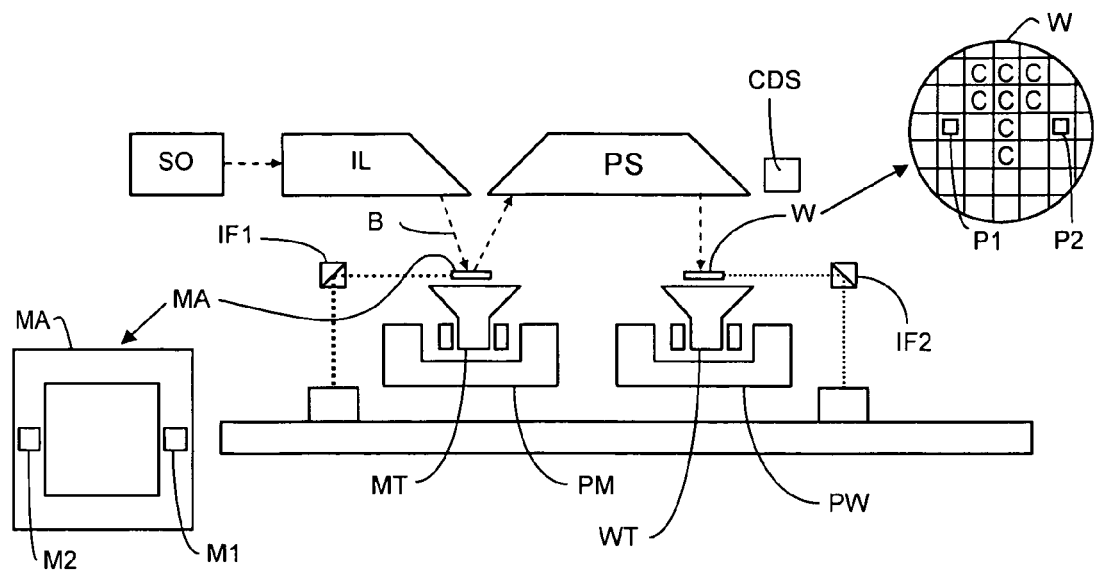
FIG. 1 depicts a lithographic apparatus which includes a contamination detection system according to an embodiment of the present invention.

FIG. 1 schematically depicts a lithographic apparatus according to one embodiment of the invention. The apparatus comprises: an illumination system (illuminator) IL configured to condition a radiation beam B (e.g. UV radiation or EUV radiation); a support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; a projection system (e.g. a refractive projection lens system) PS configured to project a pattern imparted to the radiation beam B by patterning device MA onto a target portion C (e.g. comprising one or more dies) of the substrate W; and a contamination detection system CDS configured to detect contamination of optical surfaces of the lithographic apparatus.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" as used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" as used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a reflective type (e.g. employing a reflective mask). Alternatively, the apparatus may be of a transmissive type (e.g. employing a transmissive mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

It will be appreciated that the term "optical surfaces" used herein should be broadly interpreted as encompassing any surface that radiation is directed at, and in particular optical surfaces used in the conditioning, patterning and projection of the radiation beam B. For example, the optical surfaces may be mirrors, lenses or prisms. The optical surfaces may be transmissive or reflective. A reference optical surface may be one which receives stray light (i.e. an optical surface not in the path of the radiation beam B, but one which receives light reflected (for example) from other surfaces). Properties of the optical surfaces that radiation is directed at may be inferred from properties of the reference optical surface.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system comprising, for example, suitable directing mirrors and/or a beam expander. In other cases the source may be an integral part of the lithographic apparatus, for example when the source is a mercury lamp. The source SO and the illuminator IL, together with the beam delivery system if required, may be referred to as a radiation system.

The illuminator IL may comprise an adjuster for adjusting the angular intensity distribution of the radiation beam. Generally, at least the outer and/or inner radial extent (commonly referred to as $\rho$-outer and $\rho$-inner, respectively) of the intensity distribution in a pupil plane of the illuminator can be adjusted. In addition, the illuminator IL may comprise various other components, such as an integrator and a condenser. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF2 (e.g. an interferometric device, linear encoder or capacitive sensor), the substrate table WT can be moved accurately, e.g. so as to position different target portions C in the path of the radiation beam B. Similarly, the first positioner PM and another position sensor IF1 can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Contamination of optical surfaces is a problem in lithographic apparatus, and in particular, modern optical lithography, where diffraction-limited imaging is a prerequisite. This is particularly so in EUV lithography, where carbonaceous deposits will readily form under EUV illumination. The carbonaceous deposits arise because EUV that is incident upon certain optical surfaces (e.g. mirrors) causes electrons to be emitted from the optical surfaces. Typically, these electrons have an energy of between 5 and 50 eV. It is believed that these electrons crack hydrocarbons which are present in the (EUV) lithographic apparatus. These hydrocarbons are present despite the vacuum which exists in a lithographic apparatus, due to (for example) outgassing of components in the apparatus. Over time, these cracked hydrocarbons form a carbonaceous deposit on the optical surfaces of the lithographic apparatus.

It is desirable to detect the amount of carbonaceous deposits, because such deposits will reduce the effectiveness of the optical surfaces (e.g. mirrors) of the lithographic apparatus. For example, it has been found that for some lithographic apparatus, 2.0 nanometers is the maximum thickness of carbonaceous deposit that should be allowed to form on the optical surfaces, before the presence of the deposit is too detrimental to the operation of the apparatus. It is desired to be able to detect the absolute thickness of the contaminant with high resolution.

It has been proposed to use an ellipsometric apparatus to determine the level of contaminants on the optical surfaces. Ellipsometry is a sensitive optical technique that is able to determine the level of contamination using properties of elliptically polarized light reflected from the contaminated surface. The level of contamination may be determined by using a quarter-waveplate followed by an analyzer. The orientations of the quarter-waveplate and the analyzer may be varied until no light passes through the analyzer. From these orientations the relative phase change of the light can be calculated, and from this the level (or thickness) of the contamination of the optical surface can be determined. However, a disadvantage of ellipsometry is that it is difficult to use (especially in-situ), and the experimental results are also difficult to analyze. It is also difficult to achieve a high resolution measurement using ellipsometry.

An embodiment of the present invention uses surface plasmon resonance (SPR) spectroscopy to detect the level of contamination on optical surfaces of a lithographic apparatus. Surface plasmon resonance spectroscopy as a technique may be used to detect changes in the thickness of the contaminant of a fraction of a nanometer (e.g. 0.1 nanometers or less). Furthermore, and particularly advantageously, surface plasmon resonance spectroscopy may be undertaken in-situ, allowing the level of contamination to be determined in real time without having to shut down the lithographic apparatus to perform contamination detection measurements. Being an optical technique, surface plasmon resonance has the advantage of being immune to electromagnetic field interference caused by any plasma formation and/or photoelectron emission caused by EUV radiation of optical surfaces.

Surface plasmon resonance is a non-destructive analysis technique. Surface plasmons are electron density oscillations formed at the surface of a conductor. Surface plasmons can be generated at the interface between a conductive metal film and an insulating layer by striking the metal layer with a particular type of light. A metal layer is used due to its large number of free electrons (i.e. its "sea" of electrons). The technique is often performed in a vacuum.

Surface plasmon modes may be resonantly excited in the metal layer by photons incident at a particular angle of incidence. This particular angle of incidence is mainly a characteristic of the optical constants of the materials used and the geometry of the surfaces. At a particular angle a photon incident on the metal layer will interact with a surface plasmon, and, rather than be reflected from the surface, will be coupled into the metal layer, causing a decaying evanescent field to propagate through the layer. Therefore, the interaction between the surface plasmon and the photon (excitation of the surface plasmon) results in a dip in the intensity of reflected light (specifically in the TM(p) polarized light, i.e. light with its electric field vector parallel to the plane of incidence) at a particular angle of incidence of the photons. This is observed as a dip in the angle-dependent reflectivity response of the metal layer, which is akin to a resonance at a particular angle.

As described above, properties of the surface plasmons and of the angles of incidence at which resonance occurs are highly dependent on the condition of the metallic surface, and therefore to any contamination deposited thereon. The reason for this is that the contamination of the metallic surface perturbs the decaying evanescent field at the vacuum-metal boundary, which in turn changes the angle at which surface plasmon resonance occurs. The evanescent field may be large at the boundary between the metal layer and the vacuum, leading to a high sensitivity to changes in thickness and/or refractive index of the contaminant at the interface. Thus it will be appreciated that a measured change in the resonant angle can be used to determine the amount (or thickness) of contaminant on the metallic surface. Surface plasmon resonance spectroscopy is a technique disclosed in various publications, for example in B. Liedberg, C. Nylander and I. Lundstrom, "Biosensing with surface plasmon resonance—how it all started", and Biosensors Bioelectron. 10, i-ix (1995) and J. Homola, S. S. Yee and G. Gauglitz, "Surface plasmon resonance sensors: review", Sensors and Actuators B, 54, 3-15 (1999). Therefore, mathematical details of the technique will not be described in more detail here.

Referring to FIG. 1, it can be seen that a contamination detection system CDS is positioned such that it is located away from (i.e. not in the path of) the radiation beam B, but is exposed to stray light which may be reflected from other surfaces in the lithographic apparatus. This means that the contamination detection system CDS does not obstruct or in any way intrude upon the patterning of the substrates, but is still able to measure the effect of irradiation by the radiation beam B, and therefore the build up of carbonaceous deposits on optical surfaces of the lithographic apparatus. The contamination detection system CDS uses surface plasmon resonance spectroscopy, described above, to determine the level of contamination.

Figure 2:
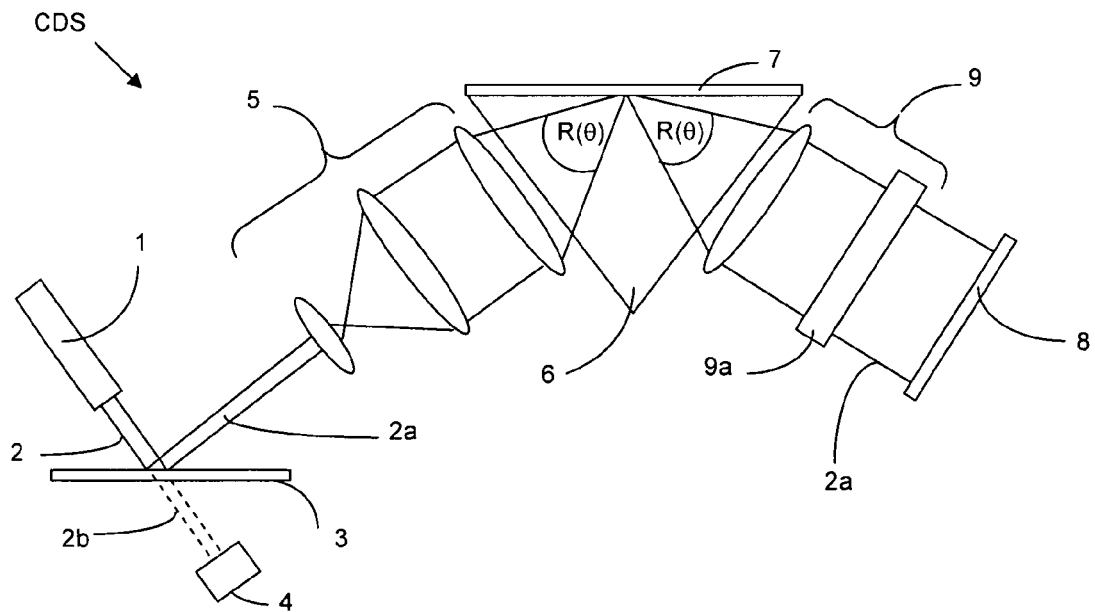
FIG. 2 depicts the contamination detection system in more detail.

The contamination detection system CDS is shown in more detail in FIG. 2. The contamination detection system CDS is a surface plasmon measurement apparatus (e.g. a surface plasmon resonance spectrometer), and is provided with a radiation source 1 which is configured to provide a beam of radiation 2, hereinafter referred to as the "probing beam 2". The probing beam 2 is directed towards a beam splitter 3, where the probing beam 2 is split into two parts, a main probing beam 2A and a reference probing beam 2B. The reference probing beam 2B is directed towards a detector 4. The intensity of the reference probing beam 2B is used as a reference level for the measurement of the thickness of the contaminant by the main probing beam 2A.

The main reference probing beam 2A is directed towards a beam expansion and focusing system 5. A polarizer (not shown) may be used to ensure the main probing beam 2A has a specific polarization. The beam expanding and focusing system 5 first expands the main probing beam 2A and then focuses the main probing beam 2A, such that the main probing beam 2A is made to pass through a prism 6 before focusing on a surface of the prism, upon which a thin metallic layer 7 has been deposited. The main probing beam 2A is then reflected from the interface between the prism 6 and the thin metallic layer 7 before it is collimated and directed towards a CCD line detector 8 by a collimation and focusing system 9. The collimation and focusing system comprises a cylindrical lens 9a, which focuses the main probing beam 2A in one dimension only, such that the main probing beam is elongate in a direction parallel to the length of the CCD line detector 8, but focused in a direction perpendicular to its length. The main probing beam 2A is not focused in two dimensions, as this would render it difficult or impossible to extract angular information therefrom. It will be appreciated that the cylindrical lens 9a can be used to focus the main probing beam 2A before or after it has reflected from the thin metallic layer 7.

The radiation source 1 is a HeNe laser, having a wavelength of 632.8 nanometers. The prism 6 is formed from fused silica. The thin layer 7 is a 50 nanometer thick silver layer. It will be appreciated that the radiation source 1 and thin metallic layer 7 may be chosen such that they are particularly suited to one another. For example, it is desirable that any dip in the reflection from the thin metallic surface 7 is particularly sharp and deep (i.e. such that it has a high figure of merit). A gold layer may be a suitable metallic surface in some circumstances, providing a high figure of merit where infra-red radiation is used to irradiate the metallic surface 7. Furthermore, it may be preferable to ensure that the prism 6 and thin metallic layer 7 are as closely matched as possible to the optical surfaces which are being used to condition, pattern and project the radiation beam B. For example, an additional two nanometer film (e.g. Ru) may be grown on top of the thin metallic layer 7 to simulate the capping layer of an EUV mirror used in EUV optical lithographic apparatus. In this way, a more accurate determination of the build up of deposits on the optical surfaces can be obtained. The thin metallic layer 7 may be deposited on top of a stacked layer of films, for multiplayer dielectric thin film stack. By using a stack of thin film layers, the line-width of the reflection dip may be decrease, and therefore the resolution of the measurement improved.

It can be seen in FIG. 2 that as the main probing beam 2A has been expanded and focused onto the interface between the prism 6 and the thin metallic layer 7; radiation impinges on the interface at a range of angles $R(\theta)$. Since a range of incident angles $R(\theta)$ is used, there is also a corresponding range of reflected angles $R(\theta)$. By using a CCD line detector 8, the effect of build up of contamination on the surface of the thin metallic layer 7 can be profiled at a range of different incident angles simultaneously. This negates the need to turn the light source or any of the optical equipment to find the above-mentioned resonant angle at which point the photons are coupled into the metallic layer and there is a dip in the reflected radiation intensity.

Figure 3:
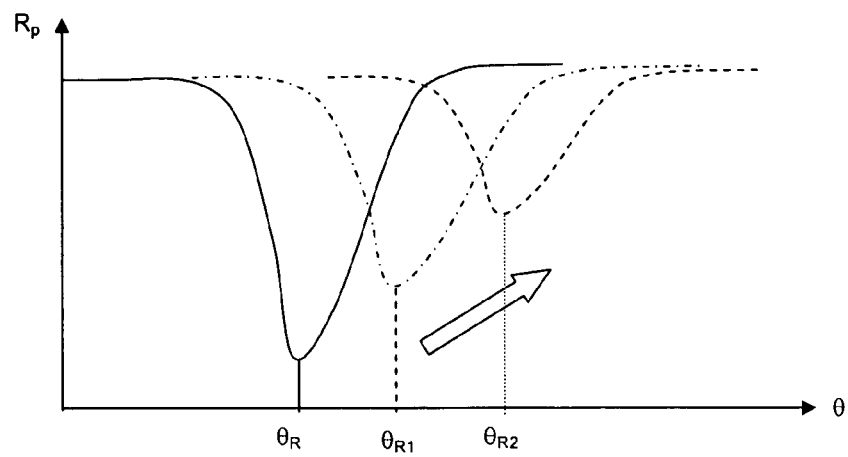
FIG. 3 depicts an operating principle of the contamination detection system of FIG. 2.

FIG. 3 illustrates how the apparatus of FIG. 2 is used. FIG. 3 is a graph of reflected intensity (specifically TM(p) polarization) verses angle of incidence of the main probing beam 2A. It can be seen that there is a significant dip in the reflected intensity at an angle of incidence of $\theta_R$ which is the resonant angle for the prism 6 and thin metallic layer 7 combination. When a carbonaceous deposit forms on the thin metallic layer 7, the conditions required for surface plasmon resonance to occur are affected, such that the resonant angle changes. It can be seen from FIG. 3 that when the amount of contaminant increases to a first level, the resonant angle is affected, and is now $\theta_{R1}$. A further increase in the thickness of the contamination layer further increases the resonant angle to $\theta_{R2}$. Thus, using the CCD line detector 8, the shift in the resonant angle can be measured and subsequently used to derive the change in thickness of the contamination layer. The level of contamination can be determined experimentally, or calculated using known mathematical relationships (and using known optical constants of the contaminant). The use of beam expansion optics 5 and a CCD line detector 8 means that no parts of the contamination detection system CDS need to be moved during operation, thereby simplifying the operation of the apparatus.

Although FIG. 3 shows the dip in reflected intensity decreasing in depth with an increase in the resonant angle, this is given by way of example only. The change in depth of the reflected intensity corresponds to more light being absorbed by an absorbent contaminant. If the contaminant is not absorptive, the depth of the intensity dip will not change.

Using surface plasmon resonance spectroscopy, the thickness of the contamination layer can be determined down to 0.1 nanometers or better, and with a resolution of much less than 0.1 nanometers.

In practice, the determination of the level of contamination may be undertaken periodically or continuously. When the deposit has been determined to exceed the desired maximum amount (for example 2.0 nanometers), atomic hydrogen (e.g. Hygrogen-1 or its isotope Hygrogen-2 (deuterium)) may be pumped into the lithographic apparatus to clean the optical surfaces. During and/or after cleaning has taken place, the contamination detection system CDS can be used to determine the (now decreased) level of contamination on the optical surfaces. When the optical surfaces have returned to their original state, this will be detected by the contamination detection system CDS from the resonant angle of the prism 6 and thin metallic layer 7 combination.

As the level of contamination can be determined to a high resolution, cleaning of the optical surfaces can be undertaken at specific intervals, and need not be undertaken unnecessarily. If cleaning is undertaken too frequently, the optical surfaces themselves may become damaged. For example, excessive cleaning may remove or otherwise damage some or all of a reflective coating on an optical surface. Excessive cleaning of the optical surfaces may also have a detrimental impact on various construction materials in the lithographic apparatus.

The above-mentioned embodiment has been described with reference to the use of a beam expansion and focusing system 5 which is used to irradiate the interface between the prism 6 and thin metallic layer 7 with radiation at a range of angles Rθ. It will be appreciated however that, while preferable, the beam expansion and focusing system 5 is not necessary, and the radiation source 1 (or other radiation manipulation device) may be moved to vary the angle of incident radiation. Instead of varying the angle of incidence of the main probing radiation beam 2A, the wavelength of radiation may be altered while keeping the angle of incidence constant. In this case, the wavelength of incident radiation is varied and a spectrum of the reflectivity as a function of wavelength is recorded whereby the spectral position of the reflection minimum is determined. The wavelength at which this minimum occurs will vary according to the amount of contaminant deposited on the thin metallic layer 7. In this way, the thickness of the layer of contaminant on the thin metallic layer 7 may be determined from the change in wavelength at which the dip in reflected radiation intensity occurs. The wavelength may be altered by using a tuneable laser as a radiation source 1, or a broadband source with a monochromator or other optical wavelength resolving device at the detection side of the system. The wavelength resolving device may comprise a dispersive (grating or prism) monochromator, a Fourier transform spectrometer, a Fabry-Perot spectrometer, or a fibre-optic analogue of these. It will be appreciated that the probing beam 2A need not be a beam, but could be a diffuse or divergent source of radiation. It will be appreciated that the radiation source 1 may emit a specific wavelength of radiation, or a range of wavelengths. It will also be appreciated that the radiation source 1 may incorporate one or more filters to control properties (e.g. the wavelength) of the probing beam 2.

Figure 4:
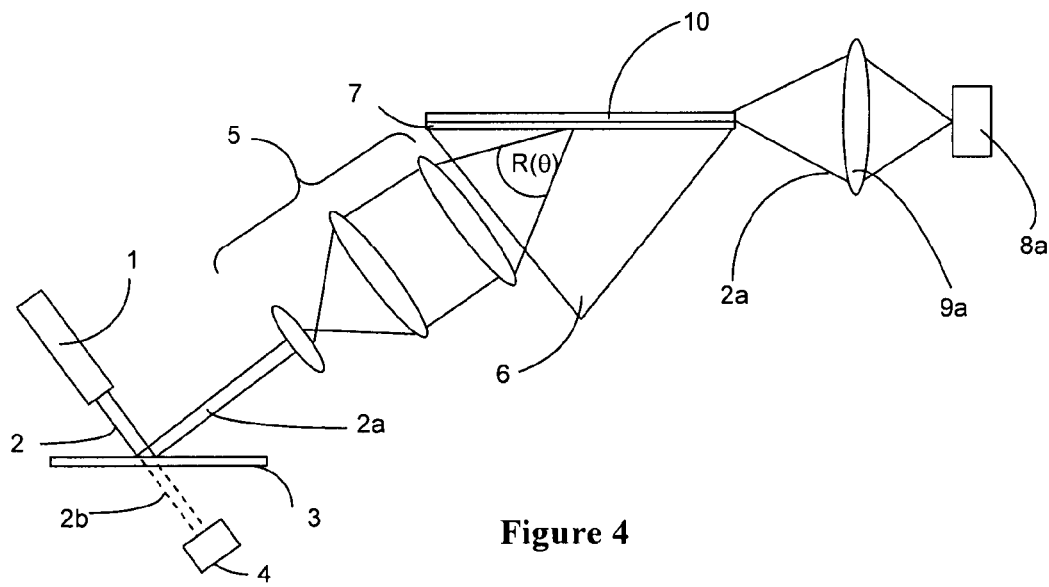
FIG. 4 depicts another embodiment of the contamination detection system.

FIG. 4 illustrates another embodiment of the contamination detection system of the present invention. The contamination detection system shown in FIG. 4 is similar to that shown in FIG. 2, and identical features have been given identical reference numbers, accordingly. The contamination detection system comprises a radiation source 1 which is arranged to direct a probing beam of radiation 2 towards a beam splitter 3. The beam splitter is arranged to split the beam of radiation 2 into a reference probing beam 2b (which is used as a reference level for the measurement of the thickness of the contaminant) and a main probing beam 2a. The main probing beam 2a is directed towards a beam expansion and focusing system 5. A polarizer (not shown) may be used to ensure that main probing beam 2a has a specific polarization. The beam expanding and focusing system 5 first expands the main probing beam 2a and then focuses the main probing beam 2a, such that the main probing beam 2a is made to pass through a prism 6 before focusing on a surface of the prism upon which a thin metallic layer 7 has been deposited.

In the contamination detection system of FIG. 2, the light reflected from the thin metallic layer 7 is detected. However, the apparatus shown in FIG. 4 differs in that a dielectric film 10 (e.g. silica) is deposited on top of the thin metallic layer 7, forming a light waveguide 10. The waveguide 10 may be planar or have a ribbed structure. The surface plasmon mode generated in the thin metallic layer 7 will couple into the dielectric waveguide 10 where it will emerge as a photon that will radiate through the waveguide 10 as a TE(s) polarized guided mode, with a decaying evanescent field outside the guide (e.g. into the vacuum or whichever environment the surface plasmon resonance spectrometer is being used in). Light radiating through the waveguide 10 is directed towards a CCD detector 8a by a lens 9a.

The coupling of incident radiation into the thin metallic layer 7 is affected by contamination forming on the surface of the waveguide 10, since the contamination causes a change in the effective refractive index of the waveguide 10. The effective change in refractive index effects the decaying evanescent field propagating through the thin metallic layer 7 and waveguide 10, and also effects the generation of plasmons in the thin metallic layer 7. Thus the contamination of the waveguide 10 affects the light coupled into the waveguide 10 from the metal layer 7, and consequently the light radiating through the waveguide 10. In summary, even though the waveguide 10 is being contaminated, it is a change in the coupling of plasmons into and out of the metallic layer 7 which allows the contamination to be detected.

A change in the frequency of the guided mode radiating through the waveguide 10 will be caused by contamination of the waveguide 10. The change in frequency may be detected optically by the CCD detector 8a. The amount or level of contamination deposited on the surface of the waveguide 10 may be determined directly using known optical constants of the contaminants, or from a process of trial and error or empirical studies.

An advantage of this embodiment is that the thin metallic layer 7 is protected from environmental attack by the dielectric layer 10. Additionally, the line-width of the guided mode radiating through the waveguide 10 is sharper (i.e. spectrally purer) than the surface plasmon mode, thus enabling a more accurate determination of the thickness of the contaminant deposit.

It will be appreciated that in the embodiment described with reference to FIG. 4 various configurations are possible. For example, the radiation source 1 may be a tuneable laser and the detector 9a a photodiode. Alternatively, a broadband source 1 can be used, and the light detected by a spectrometer and photodiode.

The waveguide 10 is located adjacent the thin metallic layer 7 (i.e. in contact with the thin metallic layer 7, or with a small gap in between) so that surface plasmons may be coupled into the waveguide 10.

If the contaminant is absorbing, then use of the surface plasmon mode to detect contamination (i.e. as described with reference to FIG. 2) is favored due to fact that the surface plasmon mode is broadened less than the guided mode in the waveguide 10. It will be appreciated that if the main probing beam 2a is incident upon the thin metallic layer 7 at the resonant angle, surface plasmon resonance will occur. In this particular embodiment, the effect of surface plasmon resonance occurring will be to cause an increase in the intensity of light coupled into the waveguide 10 and emitted from the waveguide 10.

It will be appreciated that the apparatus of FIGS. 2 and 4 could be combined such that the surface plasmon resonance mode (that described in relation to FIG. 2) and an optically guided mode (that described in relation to FIG. 4) may be detected simultaneously.

The wavelength of the probing beam 2 (and therefore probing beam 2a) may be chosen such that its frequency is resonant with an electronic or local vibration mode frequency characteristic of the particular contaminant to be monitored (e.g. carbon), i.e. so that a certain contaminant will (partly) absorb the probing beam 2a. Using such a specific wavelength allows the chemical nature of the contaminant to be confirmed, as well the amount of it which is deposited on the optical surface.

Figure 5:
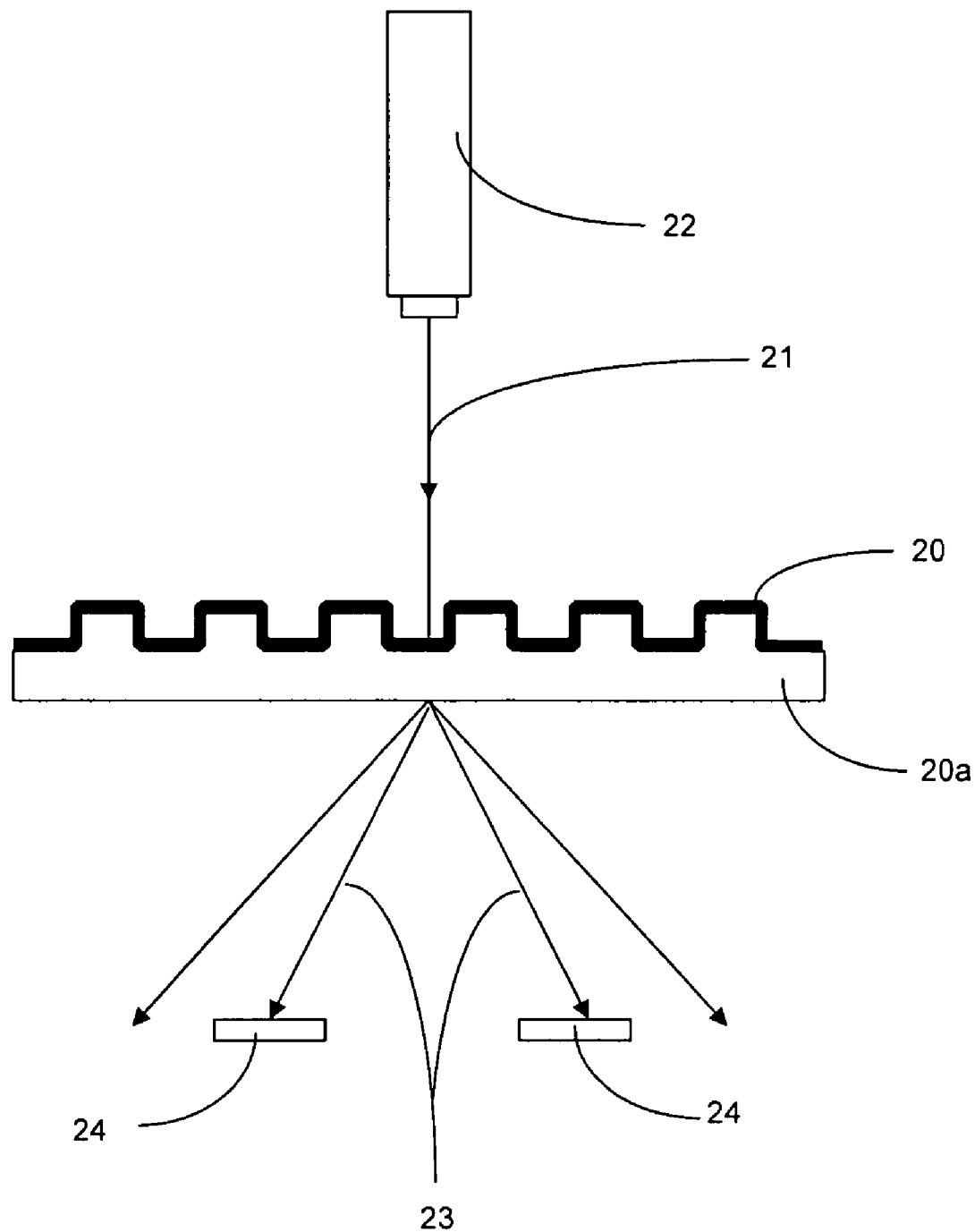
FIG. 5 depicts yet another embodiment of the contamination detection system.

FIG. 5 illustrates another embodiment of the present invention (FIG. 5 is not shown to scale). In this embodiment, surface plasmon resonance spectroscopy is undertaken using a sub-wavelength grating structure 20. A laser 22 directs a beam of radiation 21 towards the grating structure 20, such that incident radiation 21 is perpendicular to the surface of the grating 20. The sub-wavelength grating 20 is formed by depositing a thin metallic layer 20 on a glass substrate 20a which has already had the grating formed in it.

In use, the periodicity of the metal grating 20 serves to generate surface plasmon modes. The surface plasmon modes are generated when radiation is normally incident on a grating 20, obviating the need to employ oblique incident radiation through a prism (as shown in FIGS. 2 and 4, which illustrate a Kretschmann geometry). Surface plasmon modes generated in the metal layer 20 cause a decaying evanescent field to propagate through the metal layer 20 and glass substrate 20a. The surface plasmon modes are then converted to photons on the other side of the glass substrate 20a. Due to the sub-wavelength grating structure 20, the photons have been diffracted. First order diffracted photons 23 are detected by detectors 24.

The wavelength of the incident radiation 21 is scanned across a range of wavelengths until a peak is detected in the intensity of the first order diffracted light 23. This peak corresponds to the conditions for surface plasmon resonance being met, and the peak will shift for when the thickness of the contaminant changes. Thus, when contamination (not shown) builds up on or within the grooves of the grating 20, the wavelength at which surface plasmon resonance occurs will change. Therefore, by periodically irradiating the surface of the grating 20 and scanning the wavelength of the radiation, a change in the wavelength at which surface plasmon resonance occurs can be determined. From this shift in the wavelength required to generate surface plasmon resonance, the amount or level of contamination can be determined in a known manner.

It will be appreciated that instead of using a radiation beam 21 with a single wavelength, and then subsequently scanning the wavelength of this radiation beam 21, a "white" light source can be used which may comprise a range of wavelengths. A spectrometer may then be used to detect light diffracted by the sub-wavelength grating structure 20 and to determine the wavelength peak at which surface plasmon resonance occurs. This peak will shift when the grating structure 20 becomes more or less contaminated.

When radiation of a single wavelength (i.e. monochromatic radiation) is used to irradiate the surface of the grating 20, a technique known as surface enhanced Raman spectroscopy may be used to detect the chemical nature of the contamination on the grating 20. If light scattered from the surface of the grating 20 has the same energy (i.e. wavelength) as that of the incident radiation 21, the incident radiation 21 will have been elastically scattered. However, if a shift in the wavelength (i.e. energy) of the scattered light is detected (in comparison with the incident radiation 21), the incident radiation 21 will have been inelastically scattered, i.e. some of the energy will have been absorbed by contamination on the surface of the grating 20. The change in energy between the incident radiation beam 21 and scattered radiation will correspond to a vibrational mode (or other absorbing property) of the contamination. In this way, a change in the energy of the scattered light can be attributed to a characteristic property of the contamination, and therefore the chemical nature of the contamination can be determined. A change in wavelength or energy (the 'Raman shift') can be determined using a spectrometer such as a fibre coupled spectrometer, a compact grating spectrometer, a Fourier transform spectrometer, a Fabry-Perot spectrometer or any other suitable detection means.

It will be appreciated that all of the above mentioned embodiments have been described with imaging and detection apparatus in close proximity to the optical surface that has been probed. However, incident, reflected, scattered, diffracted, etc radiation may be introduced or collected using optical fibres. The use of fiber optics may permit some or all of the apparatus of the contamination detection system to be located in places remote from an optical surface. For example, a spectrometer used to detect changes in wavelengths of reflected or diffracted light may be located outside of the apparatus, whereby spectral information is provided to the spectrometer using fiber optic cables.

FIGS. 2 and 4 illustrate a contamination detection system utilizing the Kretschmann geometry. It will be appreciated that the Otto configuration may be preferable in some circumstances. Details of the Kretschmann geometry and Otto configuration can be found in, for example, A. Otto, "Excitation of nonradiative surface plasma waves in silver by the method of frustrated total reflection," Z. Phys., 216, 398 (1968), and E. Kretschmann and H. Raether, "Radiative decay of nonradiative surface plasmons excited by light," Z. Naturforsch., 23A, 2135 (1968).

The above embodiments have been described as being able to detect the chemical nature of the contamination of the optical surface. It will be appreciated that an optical surface may have deposited thereon a binding agent. This binding agent may be sensitive to (i.e. bonds with) particular chemicals. The binding agent may be chosen so that it binds to a particular contaminant. For example, the binding agent may be chosen such that long chain hydrocarbons bond with it, such that detection of the contamination of optical surface reveals the amount of the particular hydrocarbon in the system. The contamination detection system may be used to detect contamination of optical surfaces caused by a fluid that is used in immersion lithography. The fluid may be in contact with the optical surfaces or may provide contaminants (e.g. by evaporation).

It will be appreciated that surface plasmon resonance spectroscopy may be performed with incident radiation having a wavelength in the range of about 0.15 µm to 50 µm.

While the above-mentioned embodiments have been described in relation to EUV radiation, and resulting carbonaceous deposits on optical surfaces, it will be appreciated that the present invention can be used to detect the level of contamination on optical surfaces in lithographic apparatus in general. For example, the radiation used need not be EUV radiation. Furthermore, the deposits need not be carbonaceous deposits or other inorganic materials. For example, the present invention can be used to determine the build up of biological or other organic material on optical surfaces. The contamination may consist of heavy hydrocarbons generated from vacuum and resist outgassing. However, it will be appreciated that the present invention is particularly suited to optical lithographic apparatus which uses EUV radiation to expose substrates, the radiation causing the build up of carbonaceous deposits on optical surfaces to which the radiation beam B is directed.

It has been stated that an example of the maximum level of contamination is desirably 2 nanometers. It will be appreciated that this level is only an example, and that the maximum desired level may be higher or lower than 2 nanometers. The level of contamination may include the concentration of the contamination. The maximum desired level of contamination may depend on the optical surface being contaminated and/or the nature or type of contamination.

As described above, the contamination detection system CDS is located such that the thin metallic layer is exposed to stray radiation (i.e. the contamination detection system CDS is not located in the path of the radiation beam B used to expose the substrate). It will be appreciated that the contamination detection system CDS may be provided at one of a number of locations about the lithographic apparatus, and that this location may vary according to the exact layout of the lithographic apparatus and its constituent parts. The surface plasmon resonance spectrometry may be undertaken on an optical surface that the radiation beam B is directed at. However, it is preferable that the surface plasmon resonance spectrometry is undertaken on a reference optical surface located away from the radiation beam B, such that the radiation beam B is not obstructed.

Preferably, the form of the contamination detection system CDS (e.g. that of the prism 6 and thin metallic layer 7) of FIG. 2 is such that it emulates the properties of optical surfaces used to condition, pattern and project the radiation beam B. In order to fully characterize the build up of deposits on a number of optical surfaces, it may be desirable to incorporate a plurality of contamination detection system CDS. For example, each contamination detection system CDS may be constructed such that it has the same physical properties as a particular optical surface, and may be located as near to that optical surface as possible without interfering with the main radiation beam B. However, it will be appreciated by the skilled person that a single contamination detection system CDS may be sufficient for the purpose of determining the level of contamination of all optical surfaces in the lithographic apparatus in question.

It will be appreciated that the laser 1 may be replaced with any suitable radiation source. It will also be appreciated that the prism 6 may be formed from a material other than fused silica, for example any suitable glass or crystal.

The surface plasmon measurement apparatus may be any apparatus suitable for detecting surface plasmons or the effects of surface plasmons. For example, the surface plasmon measurement apparatus may be a reflectometer arranged to detect light reflected from a surface, and/or the effect that surface plasmons have on this reflected light.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured. The present invention is applicable to any lithographic apparatus where contamination of optical surfaces is a problem.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:

1. A lithographic apparatus comprising:
   at least one optical surface constructed and arranged to be exposed to a radiation beam; and
   a surface plasmon resonance measurement apparatus configured to detect contamination of the at least one optical surface,
   wherein the surface plasmon resonance measurement apparatus is adjacent to the at least one optical surface and outside a path of the radiation beam such that the measurement apparatus is exposed to stray radiation from the radiation beam without interrupting the path of the radiation beam.

2. A lithographic apparatus as described in claim 1, wherein the surface plasmon resonance measurement apparatus is a surface plasmon resonance spectrometer.

3. A lithographic apparatus as claimed in claim 1, wherein the surface plasmon resonance measurement apparatus is configured to detect contamination on a reference optical surface such that contamination of the at least one optical surface may be inferred therefrom.

4. A lithographic apparatus as claimed in claim 3, wherein the reference optical surface is located away from the radiation beam.

5. A lithographic apparatus as claimed in claim 3, wherein a waveguide is provided adjacent to the reference optical surface.

6. A lithographic apparatus as claimed in claim 3, wherein the reference optical surface is provided with a grating structure.

7. A lithographic apparatus as claimed in claim 1, wherein the surface plasmon resonance measurement apparatus is provided with a radiation source arranged to provide a probing beam of radiation to detect contamination of the optical surface.

8. A lithographic apparatus as claimed in claim 7, wherein the radiation source is configured to provide a substantially monochromatic probing beam of radiation.

9. A lithographic apparatus as claimed in claim 8, wherein the radiation source is configured to provide a probing beam of radiation having an angle of incidence which varies with respect to a reference optical surface, wherein contamination of the at least one optical surface may be inferred from detecting contamination on the reference optical surface.

10. A lithographic apparatus as claimed in claim 8, further comprising a beam expander arranged to expand the probing beam of radiation to provide a range of incident angles with respect to the reference optical surface.

11. A lithographic apparatus as claimed in claim 10, further comprising a CCD line detector arranged to detect light reflected from the reference optical surface at a range of reflected angles.

12. A lithographic apparatus as claimed in claim 7, wherein the radiation source is configured to control the wavelength of the probing beam of radiation.

13. A lithographic apparatus as claimed in claim 12, wherein the radiation source comprises a tuneable laser.

14. A lithographic apparatus as claimed in claim 1, further comprising:
    an illumination system provided with first reflective optics configured to condition an extreme ultraviolet radiation beam;
    a support constructed to support a patterning device, the patterning device being capable of imparting the extreme ultraviolet radiation beam with a pattern in its cross-section to form a patterned extreme ultraviolet radiation beam;
    a vacuum chamber to provide a vacuum beam path for the extreme ultraviolet radiation beam;
    a substrate table constructed to hold a substrate; and
    a projection system provided with second reflective optics configured to project the patterned extreme ultraviolet radiation beam onto a target portion of the substrate; and
    wherein the optical surface is part of the first or second reflective optics.

15. A method of detecting contamination of at least one optical surface of a lithographic apparatus, wherein surface plasmons of a reference optical surface located in close proximity to the at least one optical surface and outside the path of a radiation beam incident on the at least one optical surface are used to determine contamination of the at least one optical surface of the lithographic apparatus.

16. A method as claimed in claim 15, wherein contamination of the at least one optical surface is detected from an analysis of radiation reflected by the reference optical surface.

17. A method as claimed in claim 15, wherein contamination of the at least one optical surface is detected from an analysis of radiation coupled into a waveguide provided adjacent to the reference optical surface.

18. A method as claimed in claim 15, wherein contamination of the at least one optical surface is detected from an analysis of radiation scattered by the reference optical surface.

19. A method as claimed in claim 15, wherein contamination of the at least one optical surface is detected from an analysis of radiation diffracted by the reference optical surface.

20. A method as claimed in claim 15, wherein a level of contamination is detected using surface plasmons.

21. A method as claimed in claim 15, wherein the type of contamination is determined using surface plasmons.

22. A surface plasmon resonance measurement apparatus arranged to detect contamination of at least one optical surface of a lithographic apparatus, the measurement apparatus comprising a reference optical surface located outside a path of a radiation beam incident on the at least one optical surface and wherein the surface plasmon measurement apparatus is configured to detect contamination on the reference optical surface such that contamination of the at least one optical surface of the lithographic apparatus may be inferred therefrom.

23. A surface plasmon resonance measurement apparatus as claimed in claim 22, further comprising a radiation source configured to provide a probing beam of radiation, and a beam expansion system arranged to expand the probing beam of radiation to provide a range of incident angles with respect to the reference optical surface.

24. An apparatus arranged to detect contamination of an optical surface based on emulating the optical surface, the apparatus comprising:
    a surface plasmon generator arranged to generate a surface plasmon mode in a reference optical surface outside the path of a radiation beam incident on the optical surface;
    a waveguide located adjacent the reference optical surface and arranged such that the surface plasmon mode may be coupled into the waveguide and converted into a photon; and
    a detector arranged to detect the photon,
    wherein the detection of the photon assists in determining the contamination of the optical surface.

25. A surface plasmon resonance measurement apparatus as claimed in claim 22, wherein the surface plasmon resonance measurement apparatus is exposed to stray radiation from the radiation beam without interrupting the path of the radiation beam.

* * * * *